(12) United States Patent
Westlund et al.

(10) Patent No.: US 10,925,637 B2
(45) Date of Patent: Feb. 23, 2021

(54) METHODS OF IMPLANTING ELECTRODE LEADS FOR USE WITH IMPLANTABLE NEUROMUSCULAR ELECTRICAL STIMULATOR

(75) Inventors: Randy W. Westlund, River Falls, WI (US); Peter Andrew Crosby, Minneapolis, MN (US); Dan Sachs, Minneapolis, MN (US)

(73) Assignee: Mainstay Medical Limited, Dublin (IE)

( * ) Notice: Subject to any disclaimer, the term of this patent is extended or adjusted under 35 U.S.C. 154(b) by 1042 days.

(21) Appl. No.: 13/045,435

(22) Filed: Mar. 10, 2011

(65) Prior Publication Data

US 2011/0224682 A1 Sep. 15, 2011

Related U.S. Application Data

(60) Provisional application No. 61/339,943, filed on Mar. 11, 2010.

(51) Int. Cl.
| | |
|---|---|
| *A61B 17/34* | (2006.01) |
| *A61B 17/32* | (2006.01) |
| *A61B 17/00* | (2006.01) |
| *A61N 1/05* | (2006.01) |
| *A61B 90/00* | (2016.01) |

(52) U.S. Cl.
CPC ........ *A61B 17/3468* (2013.01); *A61B 90/361* (2016.02); *A61B 2017/00907* (2013.01); *A61B 2017/320044* (2013.01); *A61B 2017/320056* (2013.01); *A61N 1/0558* (2013.01)

(58) Field of Classification Search
CPC .................................................. A61B 17/3468
USPC .................................... 607/43, 117; 606/129
See application file for complete search history.

(56) References Cited

U.S. PATENT DOCUMENTS

| | | |
|---|---|---|
| 3,077,884 A | 2/1963 | Batrow et al. |
| 3,416,534 A | 12/1968 | Quinn |
| 3,710,777 A | 1/1973 | Sparks |
| 3,754,555 A | 8/1973 | Schmitt |
| 3,875,947 A | 4/1975 | Jula et al. |
| 3,893,463 A | 7/1975 | Williams |
| 3,902,501 A | 9/1975 | Citron et al. |

(Continued)

FOREIGN PATENT DOCUMENTS

| | | |
|---|---|---|
| CN | 1211930 A | 3/1999 |
| CN | 101678203 A | 3/2010 |

(Continued)

OTHER PUBLICATIONS

Garmirian et al., Disciriminating Neurogenic from Myopathic Disease via Measurement of Muscle Anisotrophy, Muscle Nerve vol. 39, No. 1, pp. 16-24 (2009) (abstract).

(Continued)

*Primary Examiner* — Richard G Louis
(74) *Attorney, Agent, or Firm* — Eversheds Sutherland (US) LLP; Christopher C. Bolten; Nicola A. Pisano

(57) ABSTRACT

Electrode leads for providing neuromuscular stimulation of the spinal muscles, and methods of implantation of electrode leads, are provided that reduce injury to target muscles, and avoid extended recuperation period, by enabling a clinician to visualize and confirm the implantation site of the electrode leads during an implantation procedure.

11 Claims, 9 Drawing Sheets

(56) References Cited

U.S. PATENT DOCUMENTS

| | | | |
|---|---|---|---|
| 3,976,082 A | 8/1976 | Schmitt | |
| 3,999,551 A | 12/1976 | Spitz et al. | |
| 4,010,757 A | 3/1977 | Jula et al. | |
| 4,026,301 A | 5/1977 | Friedman et al. | |
| 4,031,899 A | 6/1977 | Renirie | |
| 4,149,528 A | 4/1979 | Murphy | |
| 4,235,246 A | 11/1980 | Weiss | |
| 4,269,198 A | 5/1981 | Stokes | |
| 4,342,317 A | 8/1982 | Axelgaard | |
| 4,408,609 A | 10/1983 | Axelgaard | |
| 4,418,693 A | 12/1983 | Leveen et al. | |
| 4,528,984 A | 7/1985 | Morawetz et al. | |
| 4,549,556 A | 10/1985 | Tarjan et al. | |
| 4,574,806 A | 3/1986 | McCarthy | |
| 4,658,835 A | 4/1987 | Pohndorf | |
| 4,832,687 A | 5/1989 | Smith, III | |
| 4,917,093 A | 4/1990 | Dufresne et al. | |
| 5,069,680 A | 12/1991 | Grandjean | |
| 5,199,430 A | 4/1993 | Fang et al. | |
| 5,215,088 A | 6/1993 | Normann et al. | |
| 5,273,053 A | 12/1993 | Pohndorf | |
| 5,300,108 A | 4/1994 | Rebell et al. | |
| 5,330,515 A | 7/1994 | Rutecki et al. | |
| 5,496,345 A | 3/1996 | Kieturakis et al. | |
| 5,501,452 A | 3/1996 | Halvorson | |
| 5,507,788 A | 4/1996 | Lieber | |
| 5,522,854 A | 6/1996 | Ideker et al. | |
| 5,569,183 A * | 10/1996 | Kieturakis | A61B 17/00008 604/500 |
| 5,638,825 A | 6/1997 | Yamazaki et al. | |
| 5,733,307 A | 3/1998 | Dinsdale | |
| 5,741,321 A | 4/1998 | Brennen | |
| 5,782,841 A | 7/1998 | Ritz et al. | |
| 5,807,234 A | 9/1998 | Bui et al. | |
| 5,873,900 A | 2/1999 | Maurer et al. | |
| 5,916,172 A | 6/1999 | Hodges et al. | |
| 5,957,968 A | 9/1999 | Belden et al. | |
| 6,104,957 A | 8/2000 | Alo et al. | |
| 6,119,516 A | 9/2000 | Hock | |
| 6,314,325 B1 * | 11/2001 | Fitz | 607/46 |
| 6,319,241 B1 | 11/2001 | King et al. | |
| 6,324,414 B1 | 11/2001 | Gibbons et al. | |
| 6,366,819 B1 * | 4/2002 | Stokes | 607/119 |
| 6,381,496 B1 | 4/2002 | Meadows et al. | |
| 6,406,421 B1 | 6/2002 | Grandjean et al. | |
| 6,473,654 B1 | 10/2002 | Chinn | |
| 6,516,227 B1 | 2/2003 | Meadows et al. | |
| 6,527,787 B1 * | 3/2003 | Fogarty et al. | 606/159 |
| 6,565,594 B1 | 5/2003 | Herweck et al. | |
| 6,600,954 B2 | 7/2003 | Cohen et al. | |
| 6,600,956 B2 * | 7/2003 | Maschino et al. | 607/118 |
| 6,605,094 B1 | 8/2003 | Mann et al. | |
| 6,671,557 B1 | 12/2003 | Gliner | |
| 6,735,474 B1 | 5/2004 | Loeb et al. | |
| 6,839,594 B2 | 1/2005 | Cohen et al. | |
| 6,845,271 B2 | 1/2005 | Fang et al. | |
| 6,862,479 B1 | 3/2005 | Whitehurst et al. | |
| 7,018,384 B2 | 3/2006 | Skakoon | |
| 7,206,641 B2 | 4/2007 | Ignagni et al. | |
| 7,218,970 B2 | 5/2007 | Ley et al. | |
| 7,239,918 B2 | 7/2007 | Strother et al. | |
| 7,286,879 B2 | 10/2007 | Wallace | |
| 7,317,948 B1 | 1/2008 | King et al. | |
| 7,324,852 B2 | 1/2008 | Barolat et al. | |
| 7,324,853 B2 | 1/2008 | Ayal et al. | |
| 7,337,005 B2 | 2/2008 | Kim et al. | |
| 7,337,006 B2 | 2/2008 | Kim et al. | |
| 7,369,894 B2 | 5/2008 | Gerber | |
| 7,389,149 B2 | 6/2008 | Rossing et al. | |
| 7,444,181 B2 | 10/2008 | Shi et al. | |
| 7,447,546 B2 | 11/2008 | Kim et al. | |
| 7,450,993 B2 | 11/2008 | Kim et al. | |
| 7,489,561 B2 | 2/2009 | Armstrong et al. | |
| 7,493,175 B2 | 2/2009 | Cates et al. | |
| 7,499,746 B2 | 3/2009 | Buhlmann et al. | |
| 7,502,651 B2 | 3/2009 | Kim et al. | |
| 7,580,753 B2 | 8/2009 | Kim et al. | |
| 7,668,598 B2 | 2/2010 | Herregraven et al. | |
| 7,684,866 B2 | 3/2010 | Fowler et al. | |
| 7,708,763 B2 | 5/2010 | Selover et al. | |
| 7,761,166 B2 | 7/2010 | Giftakis et al. | |
| 7,792,591 B2 | 9/2010 | Rooney et al. | |
| 7,797,053 B2 | 9/2010 | Atkinson et al. | |
| 7,813,803 B2 | 10/2010 | Heruth et al. | |
| 7,908,015 B2 | 3/2011 | Lazeroms et al. | |
| 7,917,230 B2 | 3/2011 | Bly | |
| 7,930,039 B2 | 4/2011 | Olson | |
| 7,981,144 B2 | 7/2011 | Geist et al. | |
| 8,016,846 B2 | 9/2011 | McFarlin et al. | |
| 8,065,020 B2 | 11/2011 | Ley et al. | |
| 8,082,039 B2 | 12/2011 | Kim et al. | |
| 8,170,690 B2 | 5/2012 | Morgan et al. | |
| 8,229,565 B2 | 7/2012 | Kim et al. | |
| 8,229,656 B2 | 7/2012 | Ikushima et al. | |
| 8,249,701 B2 | 8/2012 | Imran et al. | |
| 8,249,713 B2 | 8/2012 | Fang et al. | |
| 8,380,318 B2 | 2/2013 | Kishawi et al. | |
| 8,391,966 B2 | 3/2013 | Luo et al. | |
| 8,409,233 B1 | 4/2013 | Chinn et al. | |
| 8,428,728 B2 | 4/2013 | Sachs | |
| 8,463,383 B2 | 6/2013 | Sakai et al. | |
| 8,498,697 B2 | 7/2013 | Yong et al. | |
| 8,606,358 B2 | 12/2013 | Sachs | |
| 8,798,005 B1 | 8/2014 | Vargantwar et al. | |
| 8,886,337 B2 | 11/2014 | Bennett et al. | |
| 8,965,516 B2 | 2/2015 | Bennett et al. | |
| 9,072,897 B2 | 7/2015 | Sachs et al. | |
| 9,079,019 B2 | 7/2015 | Crosby et al. | |
| 9,108,053 B2 | 8/2015 | Crosby et al. | |
| 9,320,847 B2 | 4/2016 | Rooney et al. | |
| 9,561,364 B2 | 2/2017 | Bondhus | |
| 9,861,811 B2 | 1/2018 | Crosby et al. | |
| 2001/0053885 A1 | 12/2001 | Gielen et al. | |
| 2002/0065543 A1 | 5/2002 | Gomperz et al. | |
| 2002/0099419 A1 | 7/2002 | Cohen et al. | |
| 2002/0147485 A1 | 10/2002 | Mamo et al. | |
| 2002/0156513 A1 * | 10/2002 | Borkan | 607/117 |
| 2002/0161415 A1 | 10/2002 | Cohen et al. | |
| 2003/0100933 A1 | 5/2003 | Ayal et al. | |
| 2003/0120328 A1 | 6/2003 | Jenkins et al. | |
| 2003/0199938 A1 | 10/2003 | Smits et al. | |
| 2004/0030360 A1 | 2/2004 | Eini et al. | |
| 2004/0111118 A1 | 6/2004 | Hill et al. | |
| 2004/0122482 A1 * | 6/2004 | Tung et al. | 607/48 |
| 2004/0214790 A1 | 10/2004 | Borgens | |
| 2004/0230281 A1 | 11/2004 | Heil et al. | |
| 2004/0236383 A1 | 11/2004 | Yelizarov | |
| 2005/0075701 A1 | 4/2005 | Shafer | |
| 2005/0080472 A1 | 4/2005 | Atkinson et al. | |
| 2005/0107861 A1 | 5/2005 | Harris et al. | |
| 2005/0119713 A1 | 6/2005 | Whitehurst et al. | |
| 2005/0149154 A1 | 7/2005 | Cohen et al. | |
| 2005/0154389 A1 * | 7/2005 | Selover et al. | 606/61 |
| 2005/0177211 A1 | 8/2005 | Leung et al. | |
| 2005/0240243 A1 | 10/2005 | Barolat et al. | |
| 2005/0246006 A1 | 11/2005 | Daniels | |
| 2005/0283204 A1 | 12/2005 | Buhlmann et al. | |
| 2006/0004429 A1 * | 1/2006 | Mrva | A61N 1/0524 607/116 |
| 2006/0009827 A1 * | 1/2006 | Kurth et al. | 607/119 |
| 2006/0032657 A1 | 2/2006 | Zarembo | |
| 2006/0052856 A1 | 3/2006 | Kim et al. | |
| 2006/0106416 A1 * | 5/2006 | Raymond | A61B 17/02 606/198 |
| 2006/0111746 A1 | 5/2006 | Foreman et al. | |
| 2006/0111754 A1 | 5/2006 | Rezai et al. | |
| 2006/0184222 A1 | 8/2006 | Camps et al. | |
| 2006/0206166 A1 | 9/2006 | Weiner | |
| 2006/0235484 A1 | 10/2006 | Jaax et al. | |
| 2006/0241716 A1 * | 10/2006 | Finch et al. | 607/43 |
| 2006/0293662 A1 * | 12/2006 | Boyer, II | A61B 17/1671 606/249 |
| 2007/0027501 A1 * | 2/2007 | Jensen | A61N 1/3605 607/45 |

(56) References Cited

U.S. PATENT DOCUMENTS

| | | |
|---|---|---|
| 2007/0049980 A1 | 3/2007 | Zielinski et al. |
| 2007/0060967 A1 | 3/2007 | Strother et al. |
| 2007/0073357 A1 | 3/2007 | Rooney et al. |
| 2007/0100377 A1 | 5/2007 | Armstrong et al. |
| 2007/0100391 A1 | 5/2007 | Armstrong |
| 2007/0100408 A1* | 5/2007 | Gerber .......................... 607/117 |
| 2007/0100411 A1 | 5/2007 | Bonde |
| 2007/0123954 A1 | 5/2007 | Gielen et al. |
| 2007/0129780 A1* | 6/2007 | Whitehurst .......... A61N 1/0556 607/118 |
| 2007/0135768 A1* | 6/2007 | Carlsen .......................... 604/158 |
| 2007/0208392 A1 | 9/2007 | Kuschner et al. |
| 2007/0239224 A1 | 10/2007 | Bennett et al. |
| 2008/0026981 A1 | 1/2008 | Muhrer et al. |
| 2008/0103573 A1 | 5/2008 | Gerber |
| 2008/0103579 A1 | 5/2008 | Gerber |
| 2008/0132961 A1* | 6/2008 | Jaax et al. .......................... 607/2 |
| 2008/0132969 A1 | 6/2008 | Bennett et al. |
| 2008/0167698 A1 | 7/2008 | Kim et al. |
| 2008/0177351 A1 | 7/2008 | Fang et al. |
| 2008/0183221 A1 | 7/2008 | Burdulis |
| 2008/0183257 A1 | 7/2008 | Imran et al. |
| 2008/0228241 A1* | 9/2008 | Sachs ................ A61N 1/36067 607/48 |
| 2008/0234791 A1 | 9/2008 | Arle et al. |
| 2008/0269716 A1 | 10/2008 | Bonde et al. |
| 2008/0269812 A1 | 10/2008 | Gerber et al. |
| 2009/0005833 A1 | 1/2009 | Cameron et al. |
| 2009/0020764 A1 | 1/2009 | Anderson et al. |
| 2009/0112263 A1* | 4/2009 | Pool et al. .................... 606/246 |
| 2009/0192567 A1 | 7/2009 | Armstrong et al. |
| 2009/0210041 A1 | 8/2009 | Kim et al. |
| 2009/0248095 A1 | 10/2009 | Schleicher et al. |
| 2009/0254095 A1 | 10/2009 | Levine et al. |
| 2009/0259280 A1 | 10/2009 | Wilkin et al. |
| 2009/0299201 A1 | 12/2009 | Gunderson |
| 2009/0326613 A1 | 12/2009 | Knoblich |
| 2010/0030227 A1* | 2/2010 | Kast et al. .................... 606/129 |
| 2010/0036280 A1 | 2/2010 | Ballegaard et al. |
| 2010/0036454 A1 | 2/2010 | Bennett et al. |
| 2010/0082086 A1* | 4/2010 | Zhu .............................. 607/117 |
| 2010/0114206 A1 | 5/2010 | Kaemmerer et al. |
| 2010/0137938 A1 | 6/2010 | Kishawi et al. |
| 2010/0152808 A1 | 6/2010 | Boggs, II |
| 2010/0152809 A1 | 6/2010 | Boggs, II |
| 2010/0174240 A1 | 7/2010 | Wells et al. |
| 2010/0179562 A1 | 7/2010 | Linker et al. |
| 2010/0185161 A1 | 7/2010 | Pellegrino et al. |
| 2010/0211149 A1 | 8/2010 | Morgan et al. |
| 2010/0249875 A1 | 9/2010 | Kishawi et al. |
| 2010/0280576 A1 | 11/2010 | Gerber et al. |
| 2010/0292769 A1 | 11/2010 | Brounstein et al. |
| 2011/0004269 A1 | 1/2011 | Strother et al. |
| 2011/0021943 A1 | 1/2011 | Lacour et al. |
| 2011/0022114 A1 | 1/2011 | Navarro |
| 2011/0022123 A1 | 1/2011 | Stancer et al. |
| 2011/0054565 A1 | 3/2011 | Wacnik et al. |
| 2011/0106207 A1 | 5/2011 | Cauller et al. |
| 2011/0190786 A1 | 8/2011 | Gerber et al. |
| 2011/0224665 A1 | 9/2011 | Crosby et al. |
| 2011/0224682 A1 | 9/2011 | Westlund et al. |
| 2011/0251662 A1 | 10/2011 | Griswold et al. |
| 2011/0257660 A1 | 10/2011 | Jones et al. |
| 2011/0270340 A1 | 11/2011 | Pellegrini et al. |
| 2012/0035953 A1 | 2/2012 | Armstrong |
| 2012/0089153 A1 | 4/2012 | Christopherson et al. |
| 2012/0116477 A1 | 5/2012 | Crowe et al. |
| 2012/0192874 A1 | 8/2012 | Bolea et al. |
| 2012/0215218 A1 | 8/2012 | Lipani |
| 2012/0283800 A1 | 11/2012 | Perryman et al. |
| 2012/0290055 A1 | 11/2012 | Boggs, II |
| 2012/0310140 A1 | 12/2012 | Kramer et al. |
| 2012/0310301 A1 | 12/2012 | Bennett et al. |
| 2012/0310302 A1 | 12/2012 | Bennett et al. |
| 2012/0310314 A1 | 12/2012 | Bennett et al. |
| 2012/0323253 A1 | 12/2012 | Garai et al. |
| 2013/0023974 A1 | 1/2013 | Amrani |
| 2013/0096641 A1 | 4/2013 | Strother et al. |
| 2013/0131766 A1 | 5/2013 | Crosby et al. |
| 2013/0155117 A1 | 6/2013 | Bang |
| 2013/0197615 A1 | 8/2013 | Rundle et al. |
| 2013/0211487 A1 | 8/2013 | Fang et al. |
| 2013/0218247 A1 | 8/2013 | Sachs |
| 2013/0238066 A1 | 9/2013 | Boggs et al. |
| 2013/0245715 A1 | 9/2013 | Peterson |
| 2013/0261696 A1 | 10/2013 | Thacker et al. |
| 2013/0296966 A1 | 11/2013 | Wongsarnpigoon et al. |
| 2013/0310901 A1 | 11/2013 | Perryman et al. |
| 2013/0338730 A1 | 12/2013 | Shiroff et al. |
| 2014/0039574 A1 | 2/2014 | Bradley |
| 2014/0046398 A1 | 2/2014 | Sachs et al. |
| 2014/0058476 A1 | 2/2014 | Crosby et al. |
| 2014/0114385 A1 | 4/2014 | Nijhuis et al. |
| 2014/0288616 A1 | 9/2014 | Rawat et al. |
| 2014/0350653 A1 | 11/2014 | Shiroff et al. |
| 2015/0105840 A1 | 4/2015 | Boggs, II |
| 2015/0306405 A1 | 10/2015 | Sachs et al. |
| 2015/0374992 A1 | 12/2015 | Crosby et al. |
| 2016/0045746 A1 | 2/2016 | Jiang et al. |
| 2016/0045747 A1 | 2/2016 | Jiang et al. |
| 2016/0067476 A1 | 3/2016 | Rawat et al. |
| 2016/0106994 A1 | 4/2016 | Crosby et al. |
| 2016/0213927 A1 | 7/2016 | McGee et al. |

FOREIGN PATENT DOCUMENTS

| | | |
|---|---|---|
| EP | 0 587 269 A2 | 3/1994 |
| EP | 1 053 762 B1 | 11/2000 |
| EP | 1 255 583 B1 | 11/2002 |
| EP | 2 125 100 A1 | 12/2009 |
| EP | 2 273 931 A1 | 1/2011 |
| WO | WO-01/58520 A1 | 8/2001 |
| WO | WO-2006/091611 A1 | 8/2006 |
| WO | WO 2006/133445 A2 | 12/2006 |
| WO | WO 2006/135791 A2 | 12/2006 |
| WO | WO 2007/051146 A1 | 5/2007 |
| WO | WO-2008/048471 A2 | 4/2008 |
| WO | WO-2008/070807 A2 | 6/2008 |
| WO | WO-2008/094952 A2 | 8/2008 |
| WO | WO-2008/112178 | 9/2008 |
| WO | WO-2009/020764 A1 | 2/2009 |
| WO | WO-2009/134475 A1 | 11/2009 |
| WO | WO-2010/062600 A2 | 6/2010 |
| WO | WO-2010/062622 A2 | 6/2010 |
| WO | WO-2011/079866 A1 | 7/2011 |
| WO | WO-2011/112773 | 9/2011 |
| WO | WO-2012/057916 A1 | 5/2012 |
| WO | WO-2012/091747 A1 | 7/2012 |
| WO | WO-2013/016268 A1 | 1/2013 |
| WO | WO-2013/019853 | 2/2013 |
| WO | WO-2013/036630 A1 | 3/2013 |
| WO | WO-2013/096260 | 6/2013 |
| WO | WO-2014/099423 A1 | 6/2014 |
| WO | WO-2015/059570 | 4/2015 |
| WO | WO-2015/187426 A1 | 12/2015 |
| WO | WO-2018/007914 A1 | 1/2018 |

OTHER PUBLICATIONS

Hodges, Is There a Role for Transversus Abdominis in Lumbo-Pelvis Stability? Manual Therapy 4(2), pp. 74-86 (1999).

Hodges et al., Intervertebral Stiffness of the Spine is Increased by Evoked Contraction of Transversus Abdominis and the Diaphragm: In Vivo Porcine Studies, Spine 28(23), pp. 2594-2601 (Dec. 1, 2003) (abstract).

Holm et al., Sensorimotor Control of the Spine, J. Electromyogr. Kinesiol. 12(3) pp. 219-234 (Jun. 2002) (abstract).

Keller et al., Muscular Contributions to Dynamic Dorsoventral Lumber Spine Stiffness, Eur. Spine J. 16(2), pp. 245-254 (Apr. 29, 2006).

Miyatani et al., Validity of Estimating Limb Muscle Volume by Bioelectrical Impedance, J. Appl. Physiol. vol. 91, pp. 386-394 (2001).

(56) References Cited

OTHER PUBLICATIONS

Rutkove, Electrical Impedance Myography: Background, Current State, and Future Directions, Muscle Nerve vol. 40, No. 6, pp. 936-946 (2009).
Solomonow et al., The Ligamento-Muscular Stabilizing System of the Spine, Spine vol. 23, No. 23, pp. 2552-2562 (1998).
Stokes et al., Surface EMG Electrodes Do Not Accurately Record from Lumbar Multifidus Muscles, Clin. Biomech. vol. 18, No. 1, pp. 9-13 (2003) (abstract).
Van Dieen et al., Trunk Muscle Recruitment Patterns, Spine vol. 28, No. 8 pp. 834-841 (2003) (abstract).
Verrills et al., Peripheral Nerve Stimulation: A Treatment for Chronic Low Back Pain and Failed Back Surgery Syndrome?, Neuromodulation: Technology at the Neural Interface, vol. 12, No. 1, pp. 68-75 (2009).
Airaksinen et al., "Chapter 4. European guidelines for the management of chronic nonspecific low back pain," European spine journal [I: official publication of the European Spine Society, the European Spinal Deformity Society, and the European Section of the Cervical Spine Research Society 15 Suppl 2 (2006):S192-300. http://www.ncbi.nlm.nih.gov/pubmed/16550448.
Baker et al., "Clinical Uses of Neuromuscular Electrical Stimulation," NeuroMuscular Electrical Stimulation—A Practical Guide, 4th ed. Rancho Los Amimgos Research and Education Institute Inc., pp. 47-66 (2000).
Bhadra et al., "Peripheral nerve stimulation for restoration of motor function," Journal of Clinical Neurophysiology: Official Publication of the American Electroencephalographic Society, 14(5):378-33 (Sep. 1997).
Bogie et al., "Effects of regular use of neuromuscular electrical stimulation on tissue health," Journal of Rehabilitation Research and Development, 40(6):469-475 (2003) available at: http://www.ncbi.nlm.nih.gov/pubmed/15077659 (Accessed Jan. 18, 2011).
Bowman et al., "Effects of Waveform Parameters on Comfort during Transcutaneous Neuromuscular Electrical Stimulation," Annals of Biomedical Engineering, 13:59-74 (1985).
Bradford et al., "Surface Electrical Stimulation in the Treatment of Idiopathic Scoliosis: Preliminary Results in 30 Patients," Spine, 8(7):757-764 (1983).
Brazier et al., "A Comparison of the EQ-5D and SF-6D Across Seven Patient Groups," Health Economics, 13:873-884 (2004).
Coghlan et al., "Electrical muscle stimulation for deep stabilizing muscles in abdominal wall," Conference proceedings: . . . Annual International Conference of the IEEE Engineering in Medicine and Biology Society. IEEE Engineering in Medicine and Biology Society. Conference, pp. 2756-2759 (2008) available at: http://www.ncbi.nlm.nih.gov/pubmed/19163276.
Coghlan et al., "Neuromuscular electrical stimulation training results in enhanced activation of spinal stabilizing muscles during spinal loading and improvements in pain ratings," Conference proceedings: . . . Annual International Conference of the IEEE Engineering in Medicine and Biology Society. IEEE Engineering in Medicine and Biology Society. Conference, pp. 7622-7625 (2011) available at: http://www.ncbi.nlm.nih.gov/pubmed/22256103.
Crago et al., "The choice of pulse duration for chronic electrical stimulation via surface, nerve, and intramuscular electrodes," Annals of Biomedical Engineering, 2(3):252-264 (1974).
Criterion Inc., "NMES Treatment Protocols," 3 pages (accessed Jun. 7, 2012) available at http://www.criterionmed.com/PDF/NMES%20Treatment%20Protocols.pdf.
Durham et al., "Surface Electrical Stimulation Versus Brace in Treatment of Idiopathic Scoliosis," Spine, 15(9):888-891 (1990).
EMPI, "Low Back Syndrome/Chronic Low Back Pain," NMES Guidelines for Treatment, 2 pages. (2003).
Ferreira et al., "Comparison of general exercise, motor control exercise and spinal manipulative therapy for chronic low back pain: A randomized trial," Pain, 131(1-2):31-37 (2007) available at: http://www.ncbi.nlm.nih.gov/pubmed/17250965.

Freeman, et al., The Role of the Lumbar Multifidus in Chronic Low Back Pain: A Review, American Academy of Physical Medicine and Rehabilitation, 2:142-146 (2010).
Friedman et al., "Electrical stimulation for scoliosis," American Family Physician, 25(4):155-160 (1982) available at: http://www.ncbi.nlm.nih.gov/pubmed/6978055 (Accessed Oct. 19, 2011).
Gazelle et al., "Tumor Ablation with radio-frequency Energy," Radiology, (2000), 217(3):633-646.
Glaser et al., "Electrical Muscle Stimulation as an Adjunct to Exercise Therapy in the Treatment of Nonacute Low Back Pain: A Randomized Trial," The Journal of Pain, 2(5):295-300 (2001).
Gondin, et al., Electromyostimulation training effects on neural drive and muscle architecture, Med. Sci. Sports. Exerc., 37(8):1291-9 (2005).
Gorman et al., "The effect of stimulus parameters on the recruitment characteristics of direct nerve stimulation," IEEE Transactions on Bio-medical Engineering, 30(7):407-414 (1983).
Haemmerich et al., "Thermal Tumor Ablation: Devices, Clinical Applications and Future Directions," Int. J. Hyperthermia, (2005) 21(8):775-760 (Abstract).
Hagg et al., "The Clinical Importance of Changes in Outcome Scores After Treatment for Chronic Low Back Pain," Eur. Spine. J., 12:12-20 (2003).
Herbert et al., "Scoliosis Treatment in Children Using a Programmable, Totally Implantable Muscle Stimulator (ESI)," IEEE Transactions on Biomedical Engineering, 36(7):801 (Jul. 1989).
Hodges et al., "Response of the deep paraspinal muscles to cortical but not transmastoid stimulation is increased at a single lumbar level following intervertebral disc lesion," Progress in Motor Control Vi—Brazil. 36:2-3 (2007).
Hortobagyi et al., "Neural adaptations to electrical stimulation strength training," European Journal of Applied Physiology, 2439-2449 (2011) available at: http://www.ncbi.nlm.nih.gov/pubmed/21643920 (Accessed Jul. 19, 2011).
Informal Response to Written Opinion for PCT/US2011/027934 dated Jan. 17, 2012.
International Search Report & Written Opinion dated Jan. 19, 2016 in Int'l PCT Patent Application No. PCT/IB2015/055926.
International Search Report & Written Opinion dated Jun. 25, 2008 in Int'l PCT Patent Appl No. PCT/US08/03126.
International Search Report and Written Opinion dated Oct. 16, 2015 in Int'l PCT Patent Appl Serial No. PCT/US2015/032732.
International Search Report for PCT/US2011/027934 dated Oct. 19, 2011.
Kiesel et al., "Measurement of lumbar multifidus muscle contraction with rehabilitative ultrasound imaging," Manual Therapy, 12(2):161-166 (2007) available at: http://www.ncbi.nlm.nih.gov/pubmed/16973400.
Lauridsen et al., "Responsiveness and Minimal Clinically Important Difference for Pain and Disability Instruments in Low Back Pain Patients," BMC Musculoskeletal Disorders, 7(82):16 pages (2006).
Lieber, Richard, Comparison between animal and human studies of skeletal muscle adaptation to chronic stimulation, Clinical Orthopaedics and related research, No. 233, pp. 19-24 (1988).
Lieber, Richard, Skeletal muscle adaptability. II: Muscle properties following spinal-cord injury, Developmental medicine and Child Neurology 28(4):533-42 (1986).
Lieber, Richard, Skeletal muscle adaptability. III: Muscle properties following chronic electrical stimulation, Developmental medicine and Child Neurology 28(5):662-70 (1986).
Mortimer et al., "Intramuscular electrical stimulation: tissue damage," Annals of Biomedical Engineering, 8(3):235-244 (1980).
Mortimer et al., "Peripheral Nerve and Muscle Stimulation. In: Horch KW, Dhillon G, eds," Neuroprosthetics: Theory and Practice (Series on Bioengineering & Biomedical Engineering—vol. 2, World Scientific Publishing Company, pp. 1-48 (2005).
Nachemson et al., "Effectiveness of Treatment with a Brace in Girls Who Have Adolescent Idiopathic Scoliosis," The Journal of Bone and Joint Surgery, 77-A(6):815-819 (Jun. 1995).
Oaao Bock, "ActiGait Implantable Drop Foot Stimulator," Surgeon Manual, 28 pages (2006).

(56) References Cited

OTHER PUBLICATIONS

O'Donnell et al., "Electrical Stimulation in the Treatment of Idiopathic Scoliosis," Clinical Orthopaedics and Related Research, No. 229:107-112 (Apr. 1988).
Paicius et al., "Peripheral Nerve Field Stimulation for the Treatment of Chronic Low Back Pain: Preliminary Results of Long-Term Follow-up: A Case Series," Neuromodulation, 10(3):279-290 (2007) available at: http://www.blackwell-synergy.com/doi/abs/10.1111/j.1525-1403.2007.00116.
Panjabi, Manohar, "A hypothesis of chronic back pain: ligament subfailure injuries lead to muscle control dysfunction," European spine journal: official publication of the European Spine Society, the European Spinal Deformity Society, and the European Section of the Cervical Spine Research Society 15, No. 5 (May 2006): 668-676. http://www.ncbi.nlm.nih.gov/pubmed/16047209.
Panjabi, Manohar, "The stabilizing system of the spine. Part 1. Function, dysfunction, adaptation, and enhancement," Journal of Spinal Disorders, 5(4)383-389 (Dec. 1992), Discussion 397. http://www.ncbi.nlm.nih.gov/pubmed/1490034.
Panjabi, Manohar, "The stabilizing system of the spine. Part II. Neutral zone and instability hypothesis," Journal of Spinal Disorders, 5(4):390-396 (Dec. 1992), Discussion 397. http://www.ncbi.nlm.nih.gov/pubmed/1490035.
Partial International Search Report dated Aug. 4, 2015 in Int'l PCT Patent Appl Serial No. PCT/US2015/032732.
PCT International Search Report & Written Opinion dated Apr. 5, 2013 in Int'l PCT Patent Application No. PCT/US2012/070259.
PCT Written Opinion dated Feb. 3, 2014 in related Int'l PCT Patent Appl No. PCT/US2012/070259.
Peckham et al., "Functional electrical stimulation for neuromuscular applications," Annual review of Biomedical Engineering, 7:327-360 (2005) available at: http://www.ncbi.nlm.nih.gov/pubmed/16004574.
Peterson et al., "Long-term intramuscular electrical activation of the phrenic nerve: safety and reliability," IEEE Transactions on Biomedical Engineering, 41(12):1115-1126 (1994).
Poitras et al., "Evidence-informed management of chronic low back pain with transcutaneous electrical nerve stimulation, interferential current, electrical muscle stimulation, ultrasound, and thermotherapy," The Spine Journal 8:226-233 (2008).
Reed B., :The Physiology of Neuromuscular Electrical Stimulation, Pediatric Physical Therapy, 9(3):96-102 (1997) available at: http://journals.lww.com/pedpt/pages/artic1eviewer.aspx?year=1997&issue=00930&article=00002&type=abstract.
Rosatelli, et al., Three-dimensional study of the musculotendinous architecture of lumbar multifidus and its functional implications, Clinical Anatomy 21(6):539-44 (2008).
RS Medical, "RS-4M Muscle Stimulator," available at http://www.rsmedical.com/documents/fact_sheet_RS4m.pdf (last visited Jul. 19, 2012).
Schwartz et al., "Therapeutic Electrical Stimulation of the Hypoglossal Nerve in Obstructive Sleep Apnea," Arch Otolaryngal Head Neck Surg., 127:1216-1223 (2001).
Sheffler et al., "Neuromuscular Electrical Stimulation in Neurorehabilitation," Muscle Nerve, 35:562-590 (2007).
Sippl, Charles J., "Computer Dictionary: Third Edition," pp. 2257 and 340.
Sluijter, "Radiofrequency Ablation in the Management of Spinal Pain," C212, (2006), IV(1):10-15.
Spinal Fusion Guidelines, MD Guidelines, 2009. www.mdguidelines.com/spinal-fusion.
Van et al., "The use of real-time ultrasound imaging for biofeedback of lumbar multifidus muscle contraction in healthy subjects," The Journal of Orthopaedic and Sports Physical Therapy, 36(12):920-925 (2006) available at: http://www.ncbi.nlm.nih.gov/pubmed/17193869.
Vrbova et al., Application of Muscle/Nerve Stimulation in Health and Disease, Springer Verlag (2008) available at: http://books.google.com/books?hl=en&lr=&id=jb8fDGxkbqEC&oi=fnd&pg=PAI&dq=Application of Muscle/Nerve Stimulation in Health and Disease&ots=CMV5rXiDQD&sig=Wg8u1YOC4PgvVDzcjdwBub5U2To (Accessed Jun. 2, 2011).
Wallwork et al., "The effect of chronic low back pain on size and contraction of the lumbar multifidus muscle," Manual Therapy, 14(5):496-500 (2009) available at: http://www.ncbi.nlm.nih.gov/pubmed/19027343.
Ward et al., "Architectural analysis and intraoperative measurements demonstrate the unique design of the multifidus for lumbar spine stability," J. Bone Joint Surg. [Am.] 91:176-185, PMC2663324 (2009).
Wikipedia, "Time-division multiplexing," https://en.wikipedia.org/wiki/Time-division_multiplexing (accessed Nov. 12, 2015).
Wright et al., "Morphologic and histochemical characteristics of skeletal muscle after long-term intramuscular electrical stimulation," Spine, 17(7):767-770 (1992) available at: http://www.ncbi.nlm.nih.gov/pubmed/1502640 (Accessed Aug. 2, 2011).
Written Opinion dated Nov. 16, 2011 in International PCT Patent Application Serial No. PCT/US2011/027934.
U.S. Appl. No. 15/202,435, filed Jul. 5, 2016, Beck et al.
U.S. Appl. No. 15/202,485, filed Jul. 5, 2016, Beck et al.
Medtronic Extension Passer 3555 Accessory Kit—Technical Instructions, 2 pages (2001).
Medtronic Interstim Therapy 3093 & 3889—Implant Manual, 38 pages (2010).
Medtronic Model 3464 Receiver/Extension Internalization Manual, SE-4 for Spinal Cord Stimulation (SCS), 7 pages (1986).
Medtronic Tunneling Rod Accessory Kit 8590-41—Technical Manual, 9 pages (No date available).
Deckers, et al., Chronic Low Back Pain: Restoration of Dynamic Stability, Neuromodulation, 18:478-486 (2015).
International Search Report & Written Opinion dated Sep. 28, 2017 in Int'l PCT Patent Appl. Serial No. PCT/IB2017/053945.
International Search Report & Written Opinion dated Oct. 20, 2017 in Int'l PCT Patent Appl. Serial No. PCT/IB2017/053946.
MicroProbes for Life Science, Nerve Cuff Electrodes, available at https://microprobes.com/products/peripheral-electrodes/nerve-cuff, accessed Mar. 5, 2018.
Unit III—The Spine, "Motions of the Spine," available at https://courses.vcu.edu/DANC291-003/unit_3.htm; accessed Mar. 5, 2018.
Wikipedia, "Anterior superior iliac spine," Updated Feb. 12, 2018, available at https://en.wikipedia.org/wiki/Anterior_superior_iliac_spine.
Wikipedia, "Blunt Dissection," Updated Feb. 14, 2018, available at https://en.wikipedia.org/wiki/Blunt_dissection.
Wikipedia, "Cavernous nerves," Updated Feb. 26, 2018, available at https://en.wikipedia.org/wiki/Cavernous_nerves.
Wikipedia, "Dorsal ramus of spinal nerve," Updated Feb. 12, 2018, available at https://en.wikipedia.org/wiki/Dorsal_ramus_of_spinal_nerve.
Wikipedia, "Ventral ramus of spinal nerve," Updated Feb. 12, 2018, available at https://en.wikipedia.org/wiki/Ventral_ramus_of_spinal_nerve.

\* cited by examiner

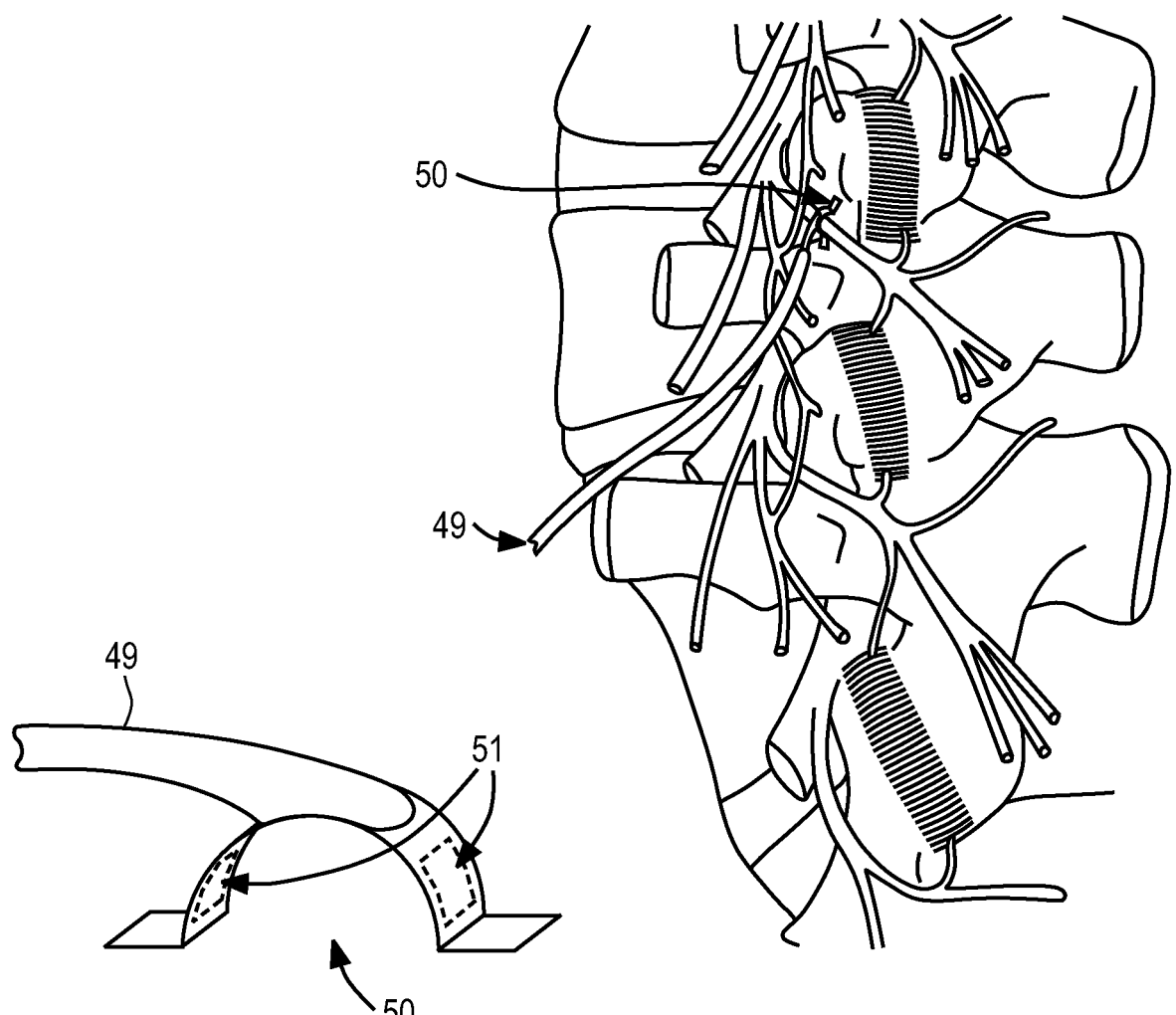
FIG. 8A
FIG. 8B
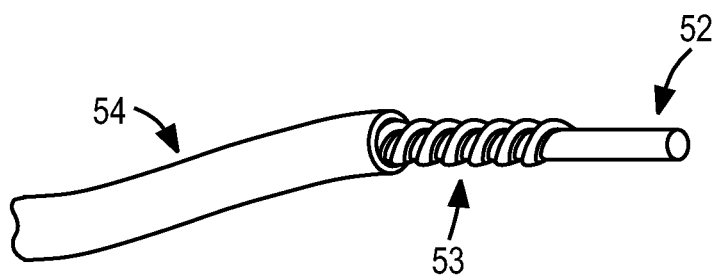
FIG. 9

Bone Fixation
Crossing Orientation

Bone Or Tissue Fixation
Adjacent Orientation

Trans Spinous Process

METHODS OF IMPLANTING ELECTRODE LEADS FOR USE WITH IMPLANTABLE NEUROMUSCULAR ELECTRICAL STIMULATOR

I. REFERENCE TO RELATED APPLICATIONS

This application claims the benefit of priority of U.S. provisional application Ser. No. 61/339,943, filed Mar. 11, 2010.

II. FIELD OF THE INVENTION

This application relates to medical devices and more particularly to a stimulator system for treating muscles and neural pathways of the back.

III. BACKGROUND OF THE INVENTION

The human lumbar spine is comprised of a spinal column consisting of vertebrae and ligaments (e.g. spinal ligaments, disc annulus, and facet capsules) and muscles that maintain spinal stabilization. It is believed that in some patients with back pain, the spinal stabilization system is dysfunctional. With soft tissue injury, mechanoreceptors may produce corrupted signals about vertebral position, motion, or loads, leading to an inappropriate muscle response.

The multifidus is the largest and most medial of the lumbar back muscles. It consists of a repeating series of fascicles which stem from the laminae and spinous processes of the vertebrae, and exhibit a constant pattern of attachments caudally. These fascicles are arranged in five overlapping groups such that each of the five lumbar vertebrae gives rise to one of these groups. At each segmental level, a fascicle arises from the base and caudolateral edge of the spinous process, and several fascicles arise, by way of a common tendon, from the caudal tip of the spinous process. Although confluent with one another at their origin, the fascicles in each group diverge caudally to assume separate attachments to the mamillary processes, the iliac crest, and the sacrum. Some of the deep fibers of the fascicles which attach to the mamillary processes attach to the capsules of the facet joints next to the mamillary processes. All the fasicles arriving from the spinous process of a given vertebra are innervated by the medial branch of the dorsal ramus that issues from below that vertebra. Each multifidus fascicle is innervated by a nerve from the medial branch of the dorsal ramus.

Training of this multifidus muscle will provide numerous benefits including improved muscle tone, endurance and strength. Further, training may improve voluntary and involuntary control of the muscles involved with spinal stabilization, eliminating lower back pain.

U.S. Patent Application Publication No. US2008/0228241 to Sachs, assigned to the assignee of the present invention, and incorporated herein in its entirety by reference, describes an implanted electrical stimulation device that is designed to restore neural drive and rehabilitate the multifidus muscle. Rather than masking pain signals while the patient's spinal stability potentially undergoes further deterioration, the stimulator system described in that application is designed to reduce the propensity for instability of the spinal column, which in turn is expected to reduce persistent or recurrent pain.

While the stimulator system described in the Sachs application seeks to rehabilitate the multifidus and restore neural drive, use of that system necessitates the implantation of one or more electrode leads in the vicinity of the patient's muscles, such as the multifidus muscles. Because surgical implantation of such electrode leads has the potential to weaken the target muscles, it would be desirable to implant the electrode leads used for neuromuscular stimulation in a manner that will not injure the target muscles, or require an extended recuperation period.

In view of the foregoing, it would be desirable to provide electrode leads and methods of implantation that avoid open surgical procedures.

It further would be desirable to provide electrode leads and methods of implantation that minimize injury to the target muscles, and avoid extended recuperation periods.

It also would be desirable to provide electrode leads and methods of implantation that permit the clinician to visualize and confirm the implantation site during the procedure.

IV. SUMMARY OF THE INVENTION

In view of the drawbacks of previously-known methods and apparatus for implanting electrode leads, the present invention provides electrode leads and methods of implantation that avoid open surgical procedures. In particular, the present invention provides electrode leads and methods of implanting such leads that reduces injury to the target muscles, and avoids extended recuperation periods. The methods of the present invention further facilitate electrode lead implantation, by enabling the clinician to visualize and confirm the implantation site of the electrode leads during the implantation procedure.

V. BRIEF DESCRIPTION OF THE DRAWINGS

FIGS. 8A and 8B are, respectively, a partial side view of a further alternative embodiment of electrode lead and a perspective view of the electrode lead located in situ.

FIG. 9 is a partial sectional view of a further alternative of an electrode lead configured to facilitate removal upon the completion of NMES therapy.

VI. DETAILED DESCRIPTION OF THE INVENTION

The present invention is directed to methods and apparatus for implanting electrode leads suitable for use with an implantable neuromuscular electrical stimulation ("NMES") device, such as described in the above-incorporated U.S. Patent Application Publication No. US2008/0228241 to Sachs. The device described in that application supplies electrical pulses to nerves innervating the spinal muscles, such as the multifidus muscle, and induces contraction of those muscles to effect a therapy designed to restore neural control and rehabilitation of the muscle. The implantable stimulator is disposed subcutaneously, and is coupled to one or more electrode leads having electrodes in contact with the target muscle, or nerves innervating the target muscles, or other anatomical structures associated with the muscle, such as ligaments and tendons. The NMES stimulation supplied by the stimulator applies a pulse regime that is very different than those employed by previously-known Spinal Cord Stimulation therapy devices, where the goal of the stimulation is simply to reduce or block the transmission of pain signals to the patient's brain, rather than rehabilitate the muscle.

While NMES electrode leads may be implanted surgically, the iatrogenic injury arising from such implantation may impede the rehabilitation process. Accordingly, the present invention is directed toward implanting the stimulation leads into muscle, fascia, ligament, or bone via surgical access and direct visualization using either minimally invasive or percutaneous techniques.

Figure 1:
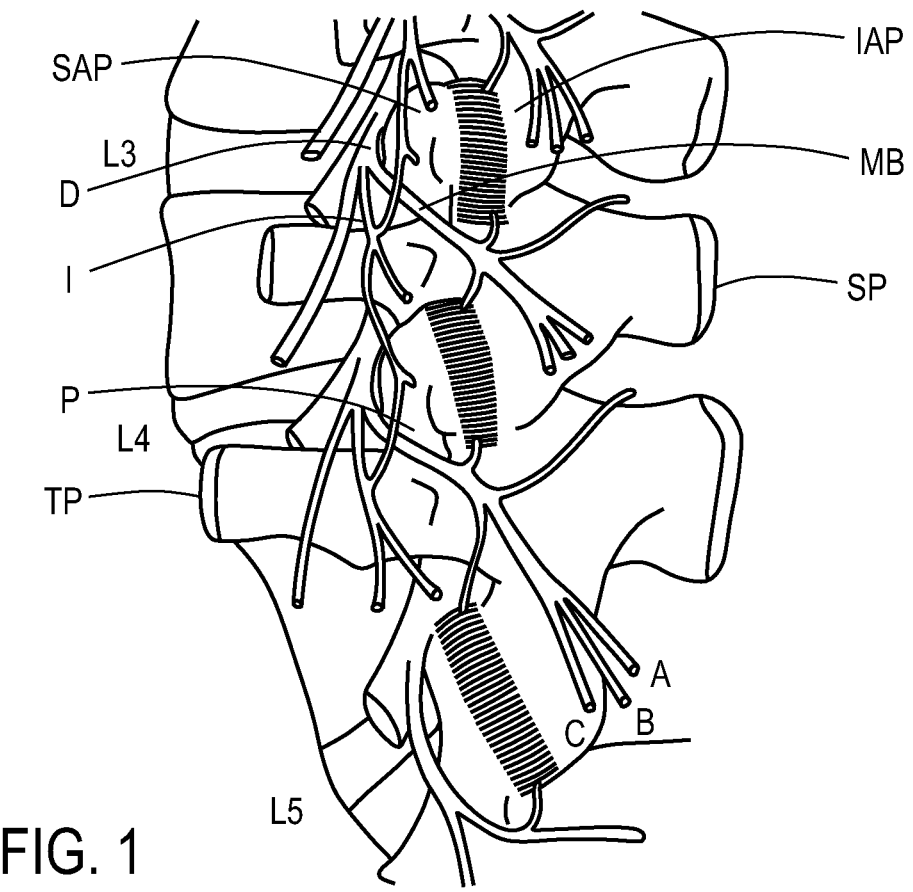
FIG. 1 is a schematic view of the lumbar portion of the human spine.

Referring to FIG. 1, the L3, L4 and L5 portions of the lumbar spine are described. The dorsal root D, dorsal ramus medial branch MB, intermediate branch I, and a representation of multifidus fascicular innervations A, B, and C are identified. Also shown in FIG. 1 are the superior articular process SAP, the spinous process SP, pedicle P, inferior anterior process IAP, and the transverse process TP.

Figure 2:
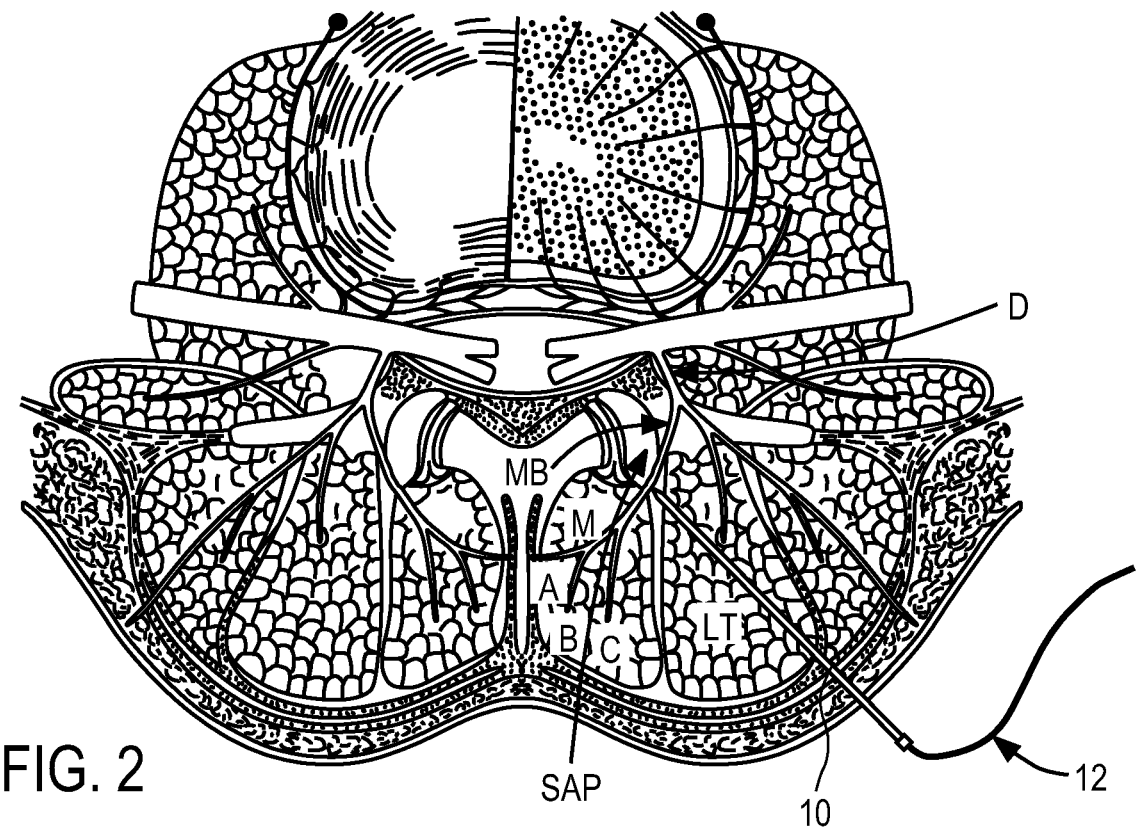
FIG. 2 is a sectional view showing a percutaneous method of implantation of an electrode lead suitable for use with a neuromuscular electrical stimulation system.

With respect to FIG. 2, percutaneous deployment of electrode lead into the spine to effect multifidus stimulation is described, and is accomplished using a large gauge hypodermic needle 10. Using fluoroscopic, acoustic, anatomic or CT guidance, needle 10 is delivered transcutaneously and transmuscularly, to the vertebra. More specifically, lead 12 then is attached to the pedicle of the vertebra or within the fascia near the medial branch of the dorsal ramus nerve. Alternatively lead 12 may be deployed into the multifidus muscle M, in the vicinity of the medial branch MB nerve, and proximal to the fascicle branches A, B and C. When deployed in this location, the NMES stimulation is expected to provide recruitment of the nerve and the multifidus fascicles.

Figure 3:
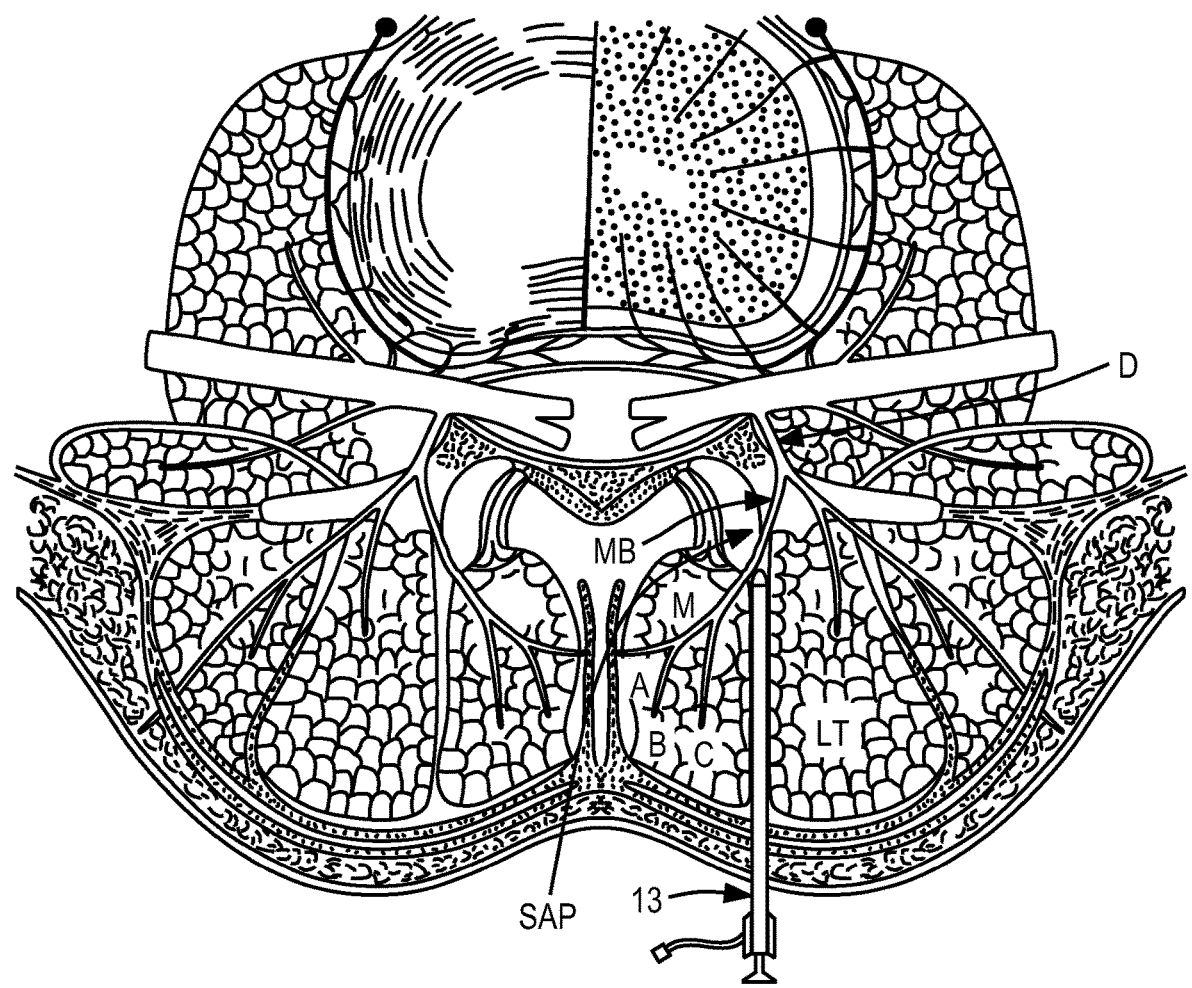
FIG. 3 is a sectional view showing a minimally invasive method of implantation of an electrode lead suitable for use with a neuromuscular electrical stimulation system.

Referring now to FIG. 3, a minimally invasive approach for implanting an electrode lead for NMES stimulation is described. In this method, a separation is formed along natural tissue planes, for example, at the plane between multifidus muscle M and longissimus muscle LT, thereby providing access to the medial branch MB. Preferably, the tissue separation is accomplished using cannula 13 having a blunt dissection tool and an endoscope, as described below. Other muscle planes, such as between the multifidus fascicles, also could be separated using the similar methods and instrumentation.

Figure 4A:
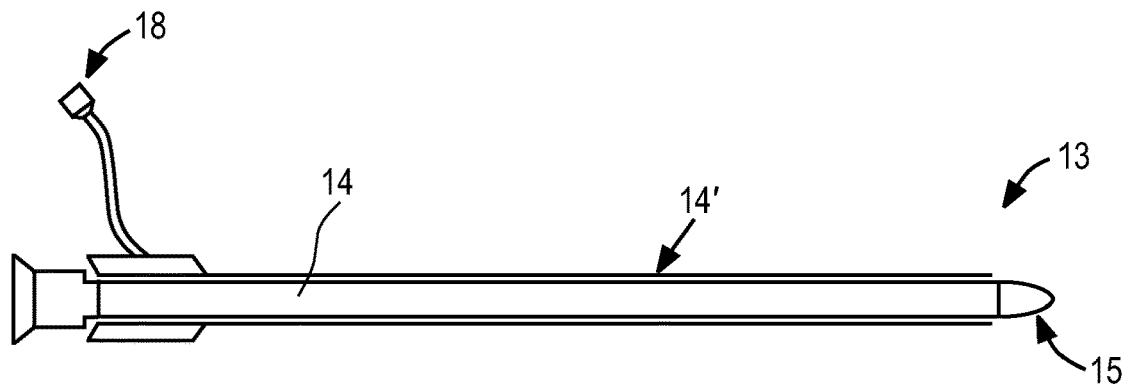
FIGS. 4A to 4E are, respectively, side and perspective views of tools and implantable electrode leads suitable for use in a minimally invasive implantation method in accordance with the principles of the present invention.

With respect to FIG. 4A, cannula 13 comprises of one or more tubes 14 and 14', transparent distal blunt dissection cone 16, through which tissue can be visualized, and side port 18 for delivery of fluids and application of vacuum. Tube 14 houses an endoscope for visualization and is fitted with tip 15 configured for blunt dissection. Tube 14' remains in position when tube 14 is removed for deployment of lead 16, depicted in FIG. 4B. The cannula for blunt dissection may have a predetermined shape suitable separating the natural tissue plane between the multifidus and longissimus muscles or be malleable such that the clinician can customize the curvature of the cannula as needed for specific patient anatomy.

Figure 4B:
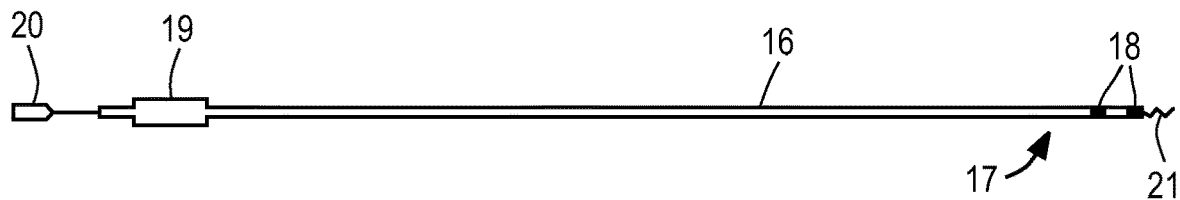
Figures 4C, 4E:
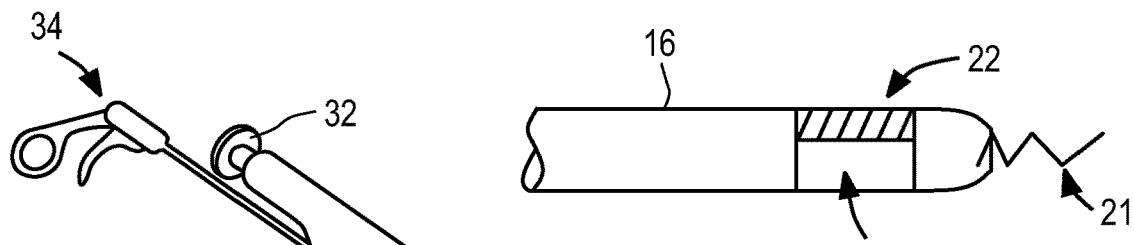

Referring to FIG. 4B, electrode lead 16 comprises of distal end 17 having two or more electrodes 18 for stimulation, and proximal end 19 for connection to an implantable stimulator or subcutaneous receiver. Distal end 17 may include two or more electrodes made of stainless steel, platinum-iridium or other suitably biocompatible material for delivery of electrical stimulation pulses. The electrodes may be cylindrical, planar or other suitable geometry, have at least 5 sq mm of surface area and may vary in length, width and diameter depending on lead body. Electrode lead 16 further may include an internal lumen that extends from proximal end 19 to distal tip 17, through which stylet 20 may be inserted. Stylet 20 may have a flat-blade tip suitable for engaging the proximal section of fixation screw 21, such that stylet 20 may be used to advance or withdraw the fixation screw by rotating the stylet. As depicted in FIG. 4C, a portion of the surface of electrode 18 may be masked with non-conductive insulating material 22, and thus used to orient the lead and direct stimulation current toward a selected nerve, e.g., the medial branch of the dorsal ramus nerve.

Figure 4D:
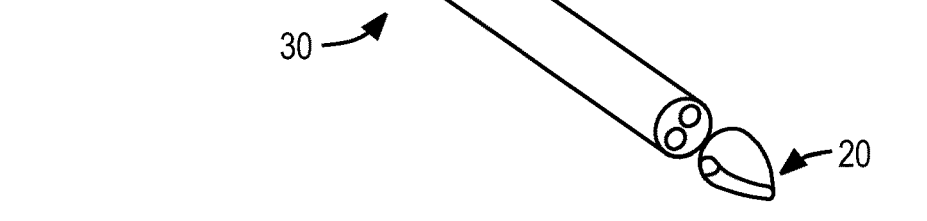

In addition, as illustrated in FIG. 4D, the body of the electrode lead need not be round. Instead electrode lead 23 has a ribbon-like cross section to facilitate passage between muscle planes, improve flex fatigue in one axis, provide better stability in vivo, and provide better guidance of stimulation current to targeted nerve(s). Proximal end 24 has an equal number of terminations as there are electrodes 25 on distal end 26, with one independent conductor for each electrode. Each termination may be connected to an output of the NMES stimulator, and each conductor coupling the terminations on the proximal end to electrodes 25 may comprise a cable or thin film structure. Electrode lead 23 also may include fixation screw 27 that is driven using removable stylet 28.

Figure 5:
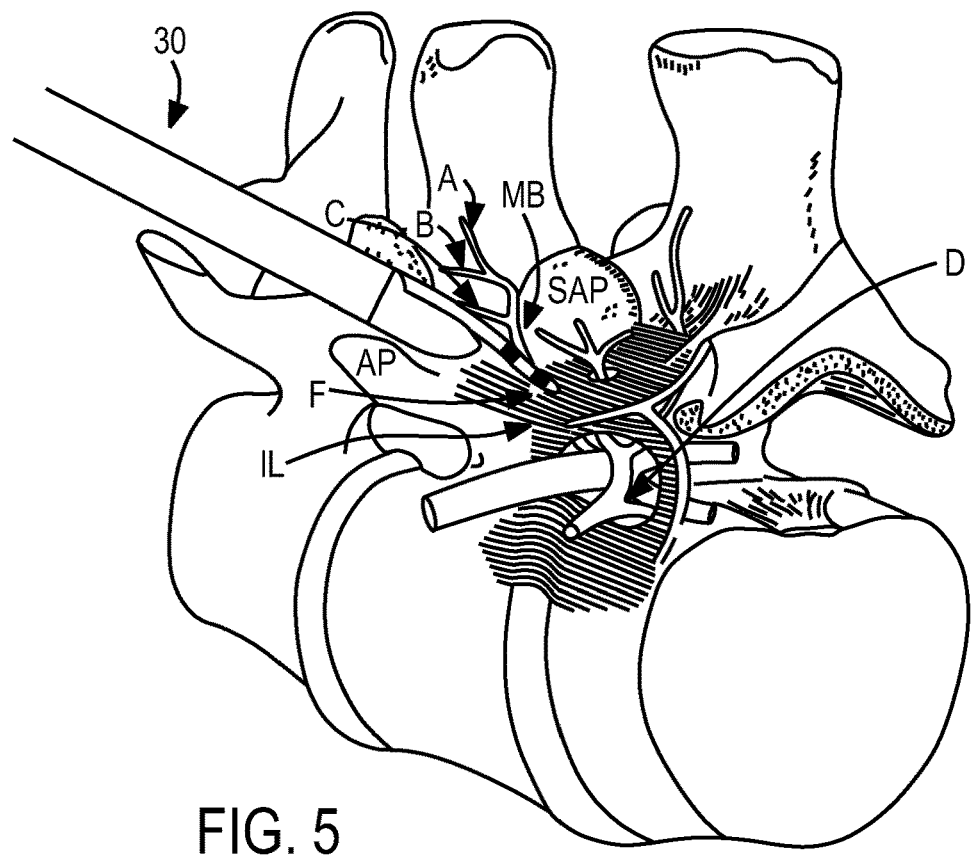
FIG. 5 is a perspective view depicting deployment of an electrode lead in the medial branch of the dorsal root of a human spine.

Referring now to FIG. 4E, alternative lead implantation cannula 30 is described. Cannula 30 is configured having a first lumen that accepts endoscope 32 and a second lumen that accepts minimally invasive surgical instrument 34, with which lead 16 or 23 may be deployed under endoscopic visualization. Cannula 30 is passed through a small incision made anterior to the natural tissue plane between the multifidus muscle M and the longissimus muscle LT. Under endoscopic visualization, a tract then is created using blunt dissection, during which tissue planes, blood vessels, ligaments, and fascia may be directly visualized using endoscope 32. Upon reaching the vertebra and visualizing superior articular process SAP, and more particularly pedicle P and medial branch MB of dorsal root D, as depicted in FIG. 5, the electrode lead is deployed. The lead may be deployed under endoscopic visualization and fixed in bone, ligament, or fascia using a fixation feature, such as corkscrew 21 above, or a suitable hook, barb or tine, as described below.

Figure 6:
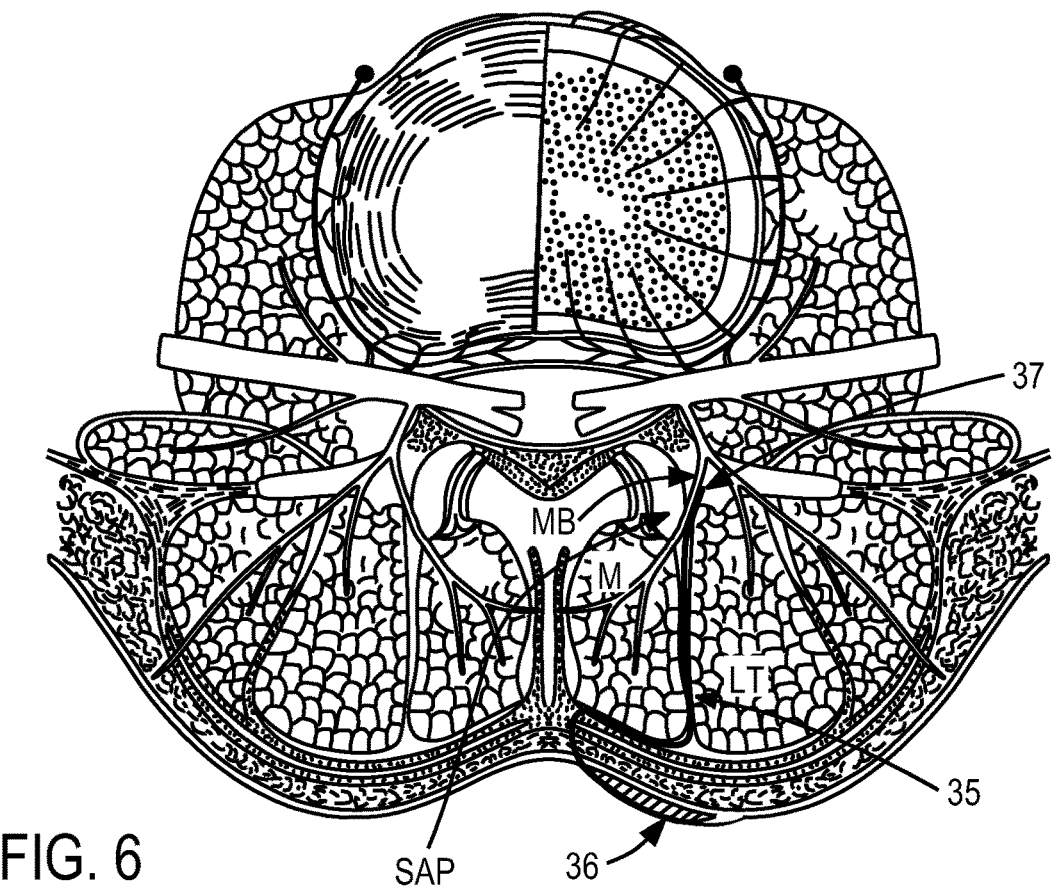
FIG. 6 is a sectional view showing an electrode lead fixed adjacent to the medial branch of the dorsal root and having its proximal end located subcutaneously.

FIG. 6 shows one possible lead configuration after implantation, in which the proximal end of an electrode lead 35 is located subcutaneously. Proximal end 36 of electrode lead 35 may include a receiver for wirelessly receiving energy using a transcutaneous energy transmission system (TETS), which are known in the art, or may be coupled to an implantable NMES stimulator, as described in the above-incorporated patent publication to Sachs. Distal tip 37 of electrode lead 35 may be fixed in the pedicle adjacent medial branch MB, such that lead 35 lies between multifidus muscle M and longissimus muscle LT. Stimulation energy from an external pulse generator may be transmitted to the subcutaneous receiver; alternatively electrode lead 35 could be tunneled subcutaneously to an implantable pulse generator.

Figure 7A:
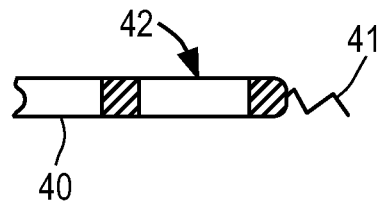
FIGS. 7A to 7E are, respectively, partial side views of various embodiments of lead fixation arrangements and a perspective view of the lead distal end when located in situ.

Whether a minimally invasive or percutaneous approach is employed, an electrode lead suitable for NMES therapy preferably includes a fixation feature that permits the distal end of the lead to be attached to the mamillary process, the anterior process, the pedicle, or locations in between. FIGS. 7A through 7E depict, respectively, various embodiments of fixation features. FIG. 7A shows electrode lead 40 having cork-screw fixation feature 41, similar to that described with respect to the embodiment of FIG. 4B, suitable for installation in a crossing orientation. In this manner of attachment, as shown in FIG. 7E, the lead crosses over the nerve. Lead 40 also may include bands 42 of polyester or other material that promotes tissue ingrowth to fasten the lead in position.

Figure 7B:
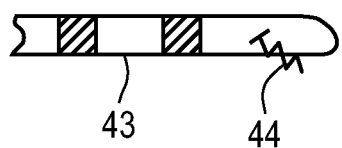
Figure 7C:
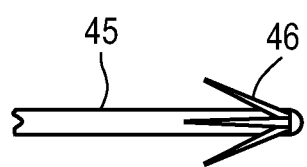
Figure 7D:
Figure 7E:
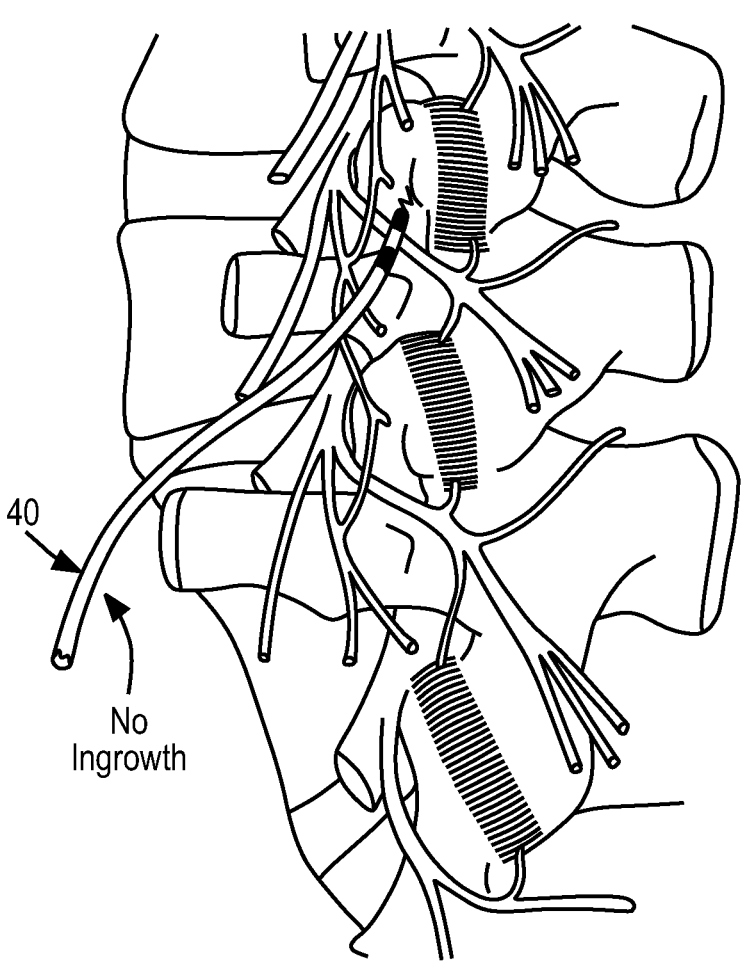

FIG. 7B shows electrode lead 43, including cork-screw fixation element 44 that exits through the side wall of the electrode lead. Lead 43 is particularly well-suited for installation in an adjacent orientation, in which the lead lies adjacent to the target nerve or muscle. FIG. 7C depicts electrode lead 45 that includes barbs 46 that may be embedded into the tissue or bone adjacent to the target nerve or tissue to retain the distal end of the electrode lead in position. Finally, FIG. 7C depicts electrode lead 47 having barb 48 that may be extended from within a lumen of the electrode lead, e.g., using a stylet, to drive the barb into the tissue or bone adjacent to the target nerve or tissue to retain the lead in position.

Referring to FIG. 8A, a further alternative embodiment of an electrode lead suitable for use in NMES therapy is described. Electrode lead 49 includes a distal region that forms bracket 50 having electrodes 51, such that bracket 50 may be disposed around a target nerve or muscle to prevent movement of the distal end of the lead, as illustrated in FIG. 8B.

Other suitable means to achieve tissue fixation include both resorbable and non-resorbable tines, and tissue hooks. Many of the same fixation features are suitable for engaging tissues like muscle, fascia or ligaments. The foregoing fixation features are intended to orient stimulation electrodes in adjacent or crossing relationships relative to the medial branch nerve. Still other means of stabilization include polymer and tissue matrix materials intended for the promotion of tissue ingrowth. Such features may take the form of polymer and metal surface treatments to create pores of appropriate diameter, polymers fabricated with pores of appropriate aperture size, and harvested or cultured cellular and extra cellular matrices that may be applied to the lead where fixation is desired.

Still other portions of the electrode leads may include materials and/or material treatments that resist tissue ingrowth, e.g., along regions of the electrode lead intended to lie between or within tissue planes that move. Materials and treatments that have pores suitable for reducing the amount and ability of tissue to become attached to the lead will make removal of the leads simpler once therapy has completed. For example, in FIG. 9, electrode lead 52 comprises flexible metal jacket 53 and outer polymeric cover 54. Flexible metal jacket 53 protects the electrode lead against trauma such as needle sticks post-implant, while polymeric cover 54 prevents tissue ingrowth, significantly improving lead removability upon completion of therapy.

Figure 10A:
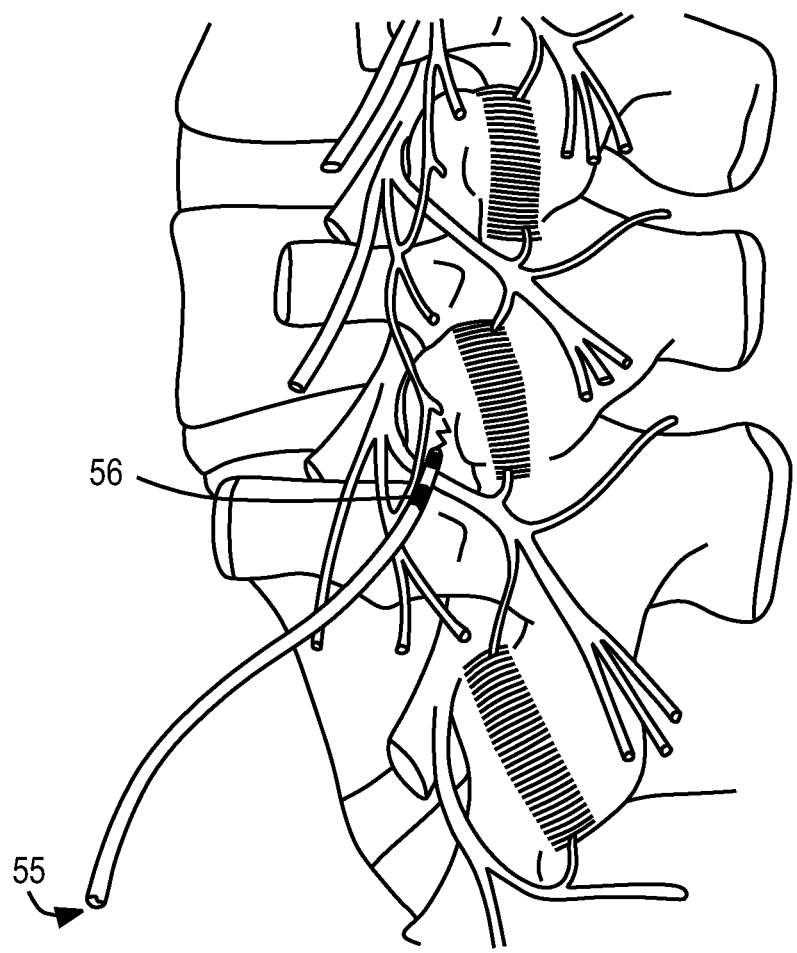
FIGS. 10A to 10C are respectively, perspective views depicting an electrode lead disposed in a crossing orientation, an adjacent orientation, and a trans-spinous orientation relative to a target nerve.
Figure 10B:
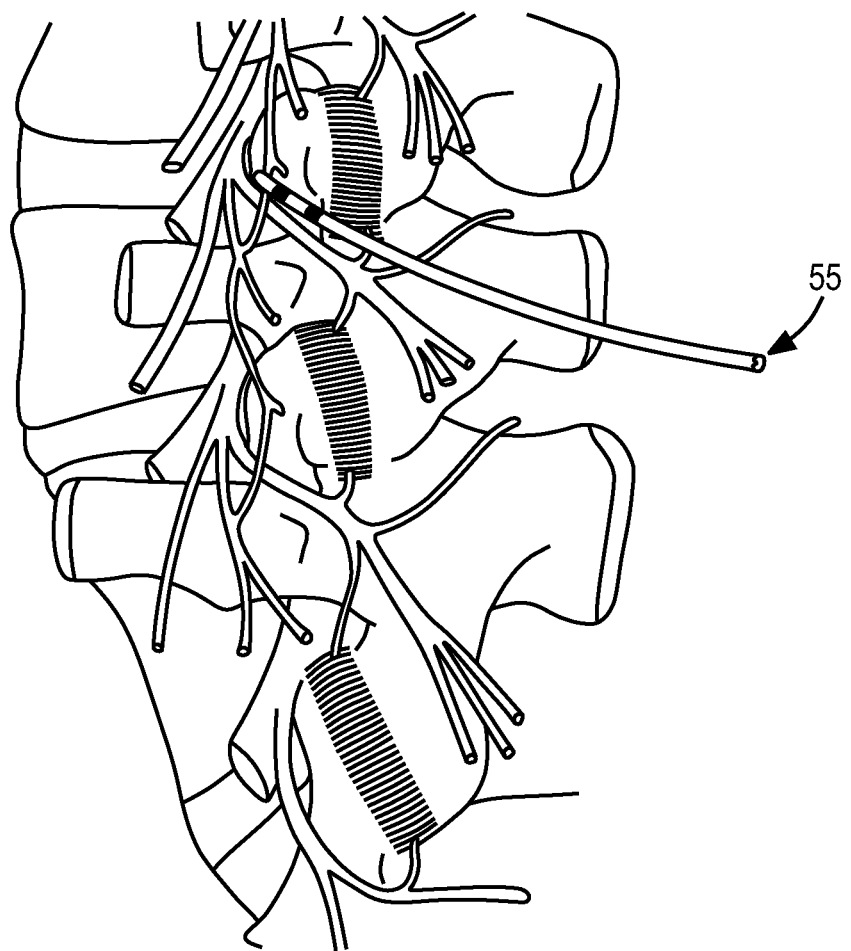
Figure 10C:
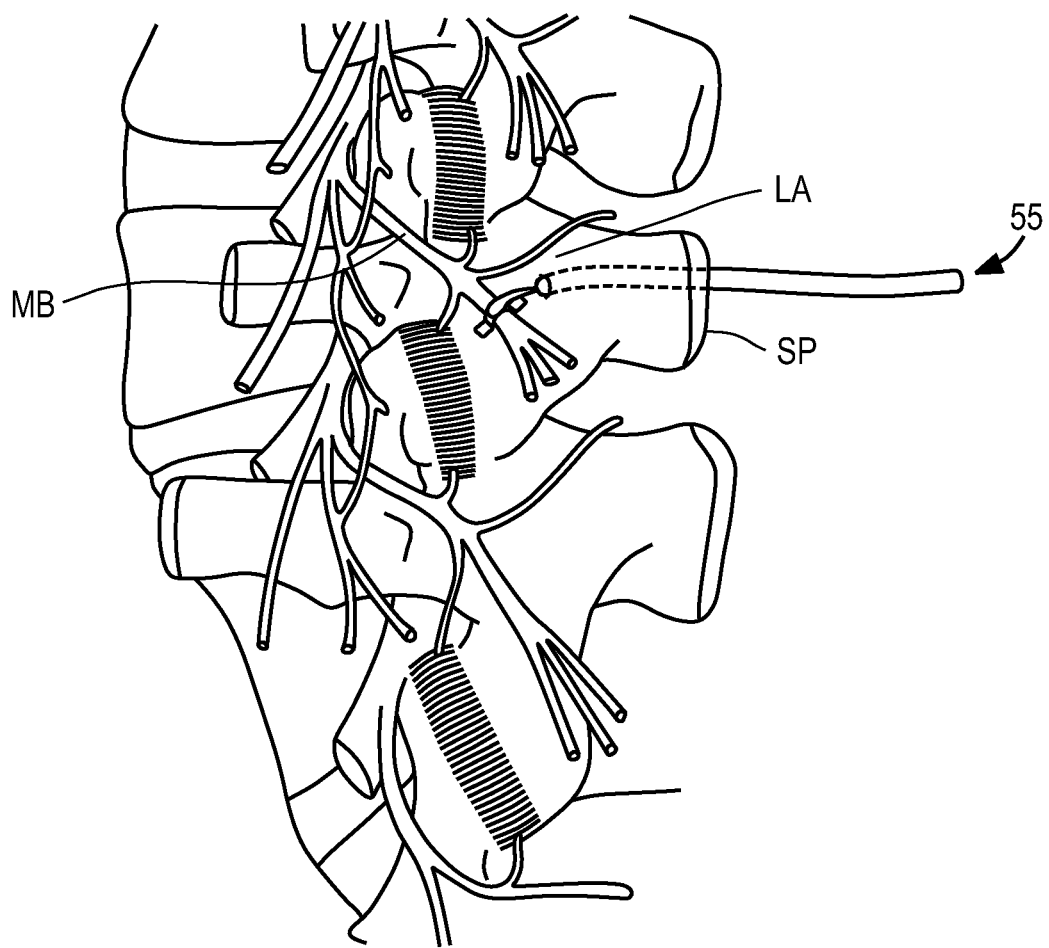

Referring to FIGS. 10A to 10C, various arrangements for disposing the electrodes of an electrode lead in relation to medial branch MB are illustrated. In FIG. 10A, lead 55 is placed so that electrodes 56 are disposed in a crossing orientation with respect to medial branch MB. In FIG. 10B, lead 55 is placed so that electrodes 56 are disposed in an adjacent orientation with respect to medial branch MB, such that lead 55 is disposed substantially parallel to a length of the nerve. In a further alternative arrangement, depicted in FIG. 10C, lead 55 is implanted as a trans-spinous process implant. In this case, a pathway is bored through spinous process SP to the area of lamina LA, exiting near medial branch MB.

FIGS. 10A to 10C depict unilateral deployment of stimulation leads to the right or left of the dorsal ramus medial branch. It should of course be understood that it is within the scope of this invention to provide bilateral stimulation training of the multifidus muscle. It further should be understood that multiple levels, for example the medial branch of the dorsal ramus L3, L4 and L5, may be implanted with leads to train the multifidus muscle to its fullest extent. While the medial branch is described as the targeted nerve for stimulation, it is within the scope of this patent that stimulation of one or more other anatomical structures such as ligaments, tendons, or nerves of other than spine stabilization muscles (e.g., transverse abdominus, psoas, interspinales, longissimus, ileocostalis, intertransversus, quadratus) may comprise adequate therapy.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed:

1. A method of implanting an electrode lead for use in neuromuscular electrical stimulation to improve muscle tone, strength or endurance, comprising:
    providing an electrode lead having a distal end including at least first and second electrodes, the electrode lead configured to be implanted with a trajectory that includes one or more multifidus fascicles;
    providing a tool for implanting the electrode lead comprising a cannula having a lumen and a tip configured for blunt dissection, the lumen configured to permit the electrode lead to extend therethrough for implantation in a vicinity of a medial branch of a dorsal ramus nerve;
    separating a multifidus muscle from a longissimus thoracis muscle along naturally occurring tissue planes therebetween using the tip of the tool to provide a path to the one or more multifidus fascicles associated with the lumbar spine; and
    implanting the distal end of the electrode lead through the lumen of the cannula in the vicinity of the medial branch of the dorsal ramus nerve.

2. The method of implanting an electrode lead of claim 1, wherein the electrode lead further comprises a fixation element.

3. The method of implanting an electrode lead of claim 1, wherein implanting the distal end of the electrode lead comprises implanting the distal end of the electrode lead with the first and second electrodes in a crossing orientation relative to the medial branch of the dorsal ramus nerve.

4. The method of implanting an electrode lead of claim 1, wherein implanting the distal end of the electrode lead further comprises implanting the distal end of the electrode lead with the first and second electrodes in an adjacent orientation relative to the medial branch of the dorsal ramus nerve.

5. The method of implanting an electrode lead of claim 1, further comprising boring an opening in a spinous process, wherein implanting the distal end of the electrode lead further comprises implanting the distal end of the electrode lead with a trans-spinous orientation relative to the medial branch of the dorsal ramus nerve.

6. A method of implanting an electrode lead for use in neuromuscular electrical stimulation of nerves innervating spinal muscles to improve muscle tone, strength or endurance, comprising:
providing an electrode lead having a distal end including a fixation element, the electrode lead configured to be implanted with a trajectory that includes one or more multifidus fascicles;
providing a tool for implanting the electrode lead comprising a cannula having a lumen and a tip configured for blunt dissection, the lumen configured to permit the electrode lead to extend therethrough for implantation in a vicinity of a medial branch of a dorsal ramus nerve;
separating muscles overlying the one or more multifidus fascicles along naturally occurring tissue planes using the tip of the tool to provide a path to a preselected portion of the medial branch of the dorsal ramus nerve;
implanting the distal end of the electrode lead with a desired relationship relative to the preselected portion through the lumen of cannula; and
deploying the fixation element to retain the distal end of the electrode lead in a vicinity of the preselected portion without penetrating the muscles overlying the one or more multifidus fascicles other than along the naturally occurring tissue planes.

7. The method of implanting an electrode lead of claim 6, wherein the overlying muscles comprise a group consisting of a transverse abdominus, interspinales, longissimus, ileocostalis, intertransversus, or quadratus muscle.

8. The method of implanting an electrode lead of claim 6, wherein the fixation element brackets the preselected portion.

9. The method of implanting an electrode lead of claim 6, wherein implanting the distal end of the electrode lead further comprises implanting the distal end of the electrode lead with a crossing orientation relative to the preselected portion.

10. The method of implanting an electrode lead of claim 6, wherein implanting the distal end of the electrode lead further comprises implanting the distal end of the electrode lead with an adjacent orientation relative to the preselected portion.

11. The method of implanting an electrode lead of claim 6, further comprising boring an opening in a spinous process, wherein implanting the distal end of the electrode lead further comprises implanting the distal end of the electrode lead with a trans-spinous orientation relative to the preselected portion.

* * * * *